United States Patent
Kotar-Jordan et al.

(10) Patent No.: US 7,662,968 B2
(45) Date of Patent: Feb. 16, 2010

(54) PROCESS FOR PREPARING LANSOPRAZOLE

(75) Inventors: Berta Kotar-Jordan, Kostanjevica na Krki (SI); Franc Vrečer, Straža pri Novem mestu (SI); Mojca Šegula Žakelj, Maribor (SI); Gregor Ritlop, Maribor (SI)

(73) Assignee: KRKA tovarna zdravil, d.d.., Novo mesto (SI)

( * ) Notice: Subject to any disclaimer, the term of this patent is extended or adjusted under 35 U.S.C. 154(b) by 308 days.

(21) Appl. No.: 11/269,211

(22) Filed: Nov. 8, 2005

(65) Prior Publication Data

US 2007/0259049 A1  Nov. 8, 2007

(30) Foreign Application Priority Data

Jan. 14, 2005  (EP) .................... 05000663

(51) Int. Cl.
  *C07D 401/12* (2006.01)
(52) U.S. Cl. .................................... 546/273.7
(58) Field of Classification Search ............... 546/273.7
  See application file for complete search history.

(56) References Cited

FOREIGN PATENT DOCUMENTS

| EP | 0302720 | 2/1989 |
|---|---|---|
| EP | 0997461 | 5/2000 |
| WO | WO 98/21201 | 5/1998 |
| WO | WO 00/72827 | 12/2000 |
| WO | WO 00/78729 | 12/2000 |
| WO | WO 02/44167 | 6/2002 |
| WO | WO/02/062786 | 8/2002 |
| WO | WO 03/082857 | 10/2003 |
| WO | WO/2004/011455 | 2/2004 |

OTHER PUBLICATIONS

Vippagunta et al., "Crystalline Solid", Advanced Drug Delivery Reviews 48 (2001) 3-26.*
Guillory (in Brittain et al.), "Polymorphism, etc.," NY: Marcel Dekker, Inc., 1999, 1-2, 183-226.*
XP-002330686, Ahn, Heon Suk et al., Modification and purification method of crystalline form of lansoprazole, Database accession No. 2004:942454 Abstract.
XP-002330687, Aihara, Kiyoshi et al., Preparation of almost anhydrous lansoprazole from its solvate and/or hydrate, Database accession No. 2004:19893 Abstract.

* cited by examiner

*Primary Examiner*—Patricia L Morris
(74) *Attorney, Agent, or Firm*—Cohen Pontani Lieberman & Pavane LLP

(57) ABSTRACT

The invention relates to a process for preparing lansoprazole. It is also directed to lansoprazole having a specific surface area and a pharmaceutical composition comprising lansoprazole.

15 Claims, 1 Drawing Sheet

Release of lansoprazole from pellets prepared according to Example 8

PROCESS FOR PREPARING LANSOPRAZOLE

1. CROSS REFERENCE TO RELATED APPLICATIONS

The present application claims priority to European Patent Application No. 05000663.4, filed Jan. 14, 2005, the entirety of which is hereby incorporated by reference.

2. FIELD OF THE INVENTION

The present invention relates to a process for preparing lansoprazole. It is also directed to lansoprazole having a specific surface area and a pharmaceutical composition comprising lansoprazole.

BACKGROUND OF THE INVENTION

Lansoprazole is the generic name for 2-[[[3-methyl-4-(2,2,2-trifluoroethoxy)-2-pyridinyl]methyl]sulfinyl]-1H-benzimidazole and it has the following formula (I):

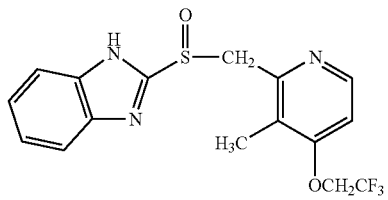

(I)

Lansoprazole is a well-known gastric proton pump inhibitor and thus it can inhibit gastric acid secretion and is used as an antiulcer agent.

Processes for preparing lansoprazole are known. Several methods involve the use of a lansoprazole precursor having a thioether group which is subjected to an oxidation.

EP 0 174 726 B1 discloses the use of a peracid such as m-chloroperbenzoic acid, sodium bromite, sodium hypochlorite or hydrogen peroxide as an oxidizing agent. The oxidation is carried out in halogenated hydrocarbons, amides, alcohols or mixtures thereof.

EP 0 302 720 A1 describes a process for preparing lansoprazole using hydrogen peroxide in the presence of a vanadium compound such as vanadium pentoxide, sodium metavanadate or vanadium acetylacetonate.

According to WO 02/062786 A1 lansoprazole is prepared by using tert-butyl hydroperoxide (TBHP) in the presence of vanadium pentoxide, sodium metavanadate or vanadium acetylacetonate. Preferably, the oxidation is performed in toluene or isopropanol.

WO 2004/011455 A1 discloses a process for preparing lansoprazole using tert-butyl hydroperoxide (TBHP) in the presence of vanadium oxytrichloride as catalyst wherein the reaction is carried out in a solvent such as a $C_1$- to $C_5$-alcohol, decane, nonane, toluene or a mixture with water. The vanadium oxytrichloride is used in the presence of an alcohol. Moreover, the reaction is preferably performed in the presence of a weak base. Crude lansoprazole is obtained in a yield of at most 90%.

WO 03/008406 A1 refers to a process for preparing benzimidazole-type compounds by reacting a corresponding precursor with an oxidizing agent in a suitable solvent, extracting the sulphone by-product and isolating the product. Preferably, m-chloroperbenzoic acid is used as oxidizing agent.

The processes according to the prior art for preparing lansoprazole suffer from a low yield of the produced lansoprazole as well as a high content of impurities of the lansoprazole. This may be due to the fact that the selectivity in the oxidation step is low and thus by-products such as the corresponding benzimidazole N-oxide and the corresponding sulphone can be formed by an oxidation of the nitrogen and an overoxidation of the sulfide, respectively. When scaling-up the processes according to the prior art, the control of impurities is even more difficult resulting in extensive isolation procedures in order to obtain pure lansoprazole.

Consequently, there is still a need for an improved process for preparing lansoprazole avoiding the afore-mentioned drawbacks. In addition to that it will be highly advantageous, if solid lansoprazole is provided which is quickly released from a pharmaceutical composition.

These problems are surprisingly solved by the present invention.

Figure 1:
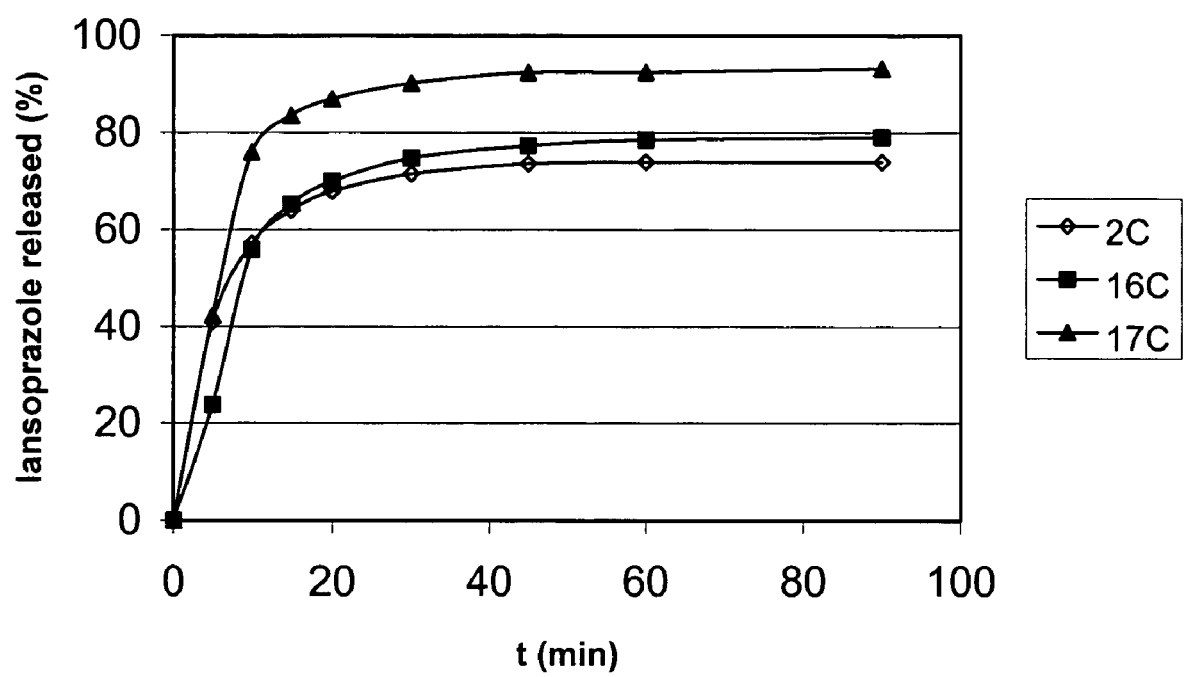
FIG. 1 shows the amount of lansoprazole released over time for pellets having different surface areas.

2C: pellets comprising lansoprazole having a BET-surface area of 0.87 $m_2$/g (prepared according to Example 3), 16C: pellets comprising lansoprazole having a BET-surface area of 1.00 $m_2$/g (prepared according to Example 5), 17C: pellets comprising lansoprazole having a BET-surface area of 4.67 $m_2$/g (prepared according to Example 4).

DETAILED DESCRIPTION OF THE PRESENTLY PREFERRED EMBODIMENTS

The process according to the invention for preparing lansoprazole which is represented by formula (I)

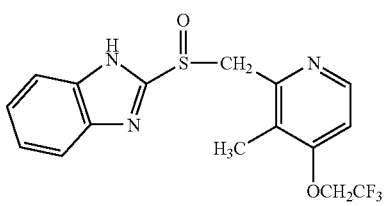

(I)

comprises
(a) reacting a compound of formula (II)

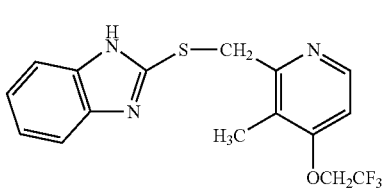

(II)

or a hydrate, solvate or salt thereof with an oxidizing agent in the presence of
(A) a vanadium catalyst selected from the group consisting of vanadium(V) oxytrifluoride, vanadium(V) triesters and mixtures thereof and/or
(B) acetanhydride, and
(b) optionally recovering the lansoprazole.

It has surprisingly been found that the use of a specific vanadium catalyst selected from the group consisting of vanadium(V) oxytrifluoride, vanadium(V) triesters, such as vanadium(V) oxytriethoxide, vanadium(V) trioxypropoxide and vanadium(V) oxytriisopropoxide, and mixtures thereof and/or the use of acetanhydride allows the production of lansoprazole in high yields and leads to lansoprazole which contains only small amounts of impurities, even in a high scale production.

In step (a) of the process according to the invention a compound of formula (II) or a derivative thereof is reacted. Preferably, a hydrate of compound (II) is used which can be obtained by the following reaction scheme:

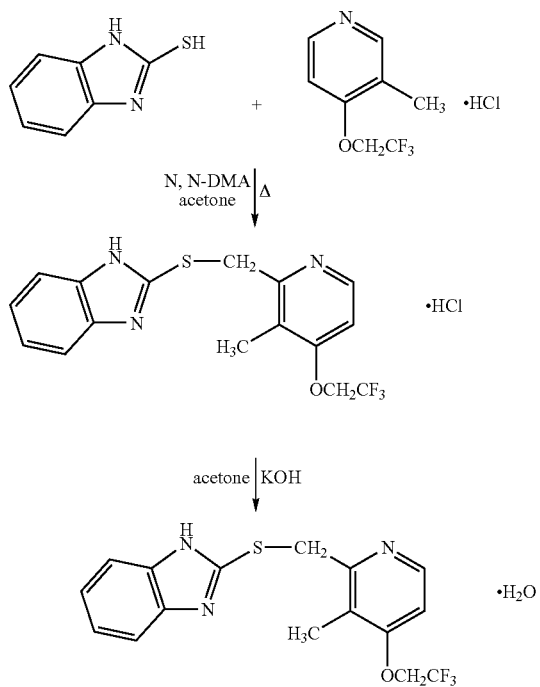

In the process according to the invention the oxidation of the thioether group of the compound of formula (II), a hydrate, solvate or salt thereof is effected by an oxidizing agent. It is possible to use 3-chloroperbenzoic acid. However, the oxidizing agent is preferably selected from hydrogen peroxide or a source of hydrogen peroxide. Particularly preferred is the use of an urea adduct of hydrogen peroxide as a source of hydrogen peroxide.

The amount of the oxidizing agent used is generally about 0.5 to 3.0 equivalents, preferably 0.7 to 2.0 equivalents and most preferably 0.9 to 1.5 equivalents relative to compound (II).

The reaction mixture of step (a) further comprises a vanadium compound and/or acetanhydride. The vanadium catalyst is selected from the group consisting of vanadium(V) oxytrifluoride, vanadium(V) triesters, such as vanadium(V) oxytriethoxide, vanadium(V) trioxypropoxide and vanadium (V) oxytriisopropoxide, and mixtures thereof. Preferably, vanadium(V) oxytriisopropoxide is used.

The amount of the vanadium catalyst is usually about 0.001 to 0.05 equivalents, preferably 0.002 to 0.02 equivalents and most preferred 0.005 to 0.015 equivalents relative to compound (II). The amount of acetanhydride is usually about 0.5 to 2.0 equivalents, and preferably 0.5 to 1.0 equivalents relative to compound (II).

Furthermore, step (a) is usually carried out in an organic solvent. Preferably, this solvent is selected from the group consisting of 1-methyl-2-pyrrolidone, N,N-dimethylacetamide, N,N-dimethylformamide, alcohols and mixtures thereof. In particular, 1-methyl-2-pyrrolidone is used as solvent.

It has been found out, that the intermediates as well as the product are highly soluble in the solvents preferably used according to the invention. Thus, it is possible to carry out the process for the preparation of lansoprazole in a concentrated solution which is also beneficial for a scaling-up of the process. In a preferred embodiment, the concentration of lansoprazole in the reaction mixture of step (a) is from 10 to 30% by weight at the end of the reaction.

It has proven particularly preferred that first the compound of formula (II) or a derivative thereof is dissolved in the organic solvent at room temperature, then the catalyst is added and the reaction mixture is cooled to a temperature of 0 to 5° C. Finally, the reaction is started by the addition of the oxidizing agent and the reaction is carried out at a temperature of 0 to 20° C., preferably 0 to 10° C.

Preferably, the reaction of step (a) is performed for 1 to 5 hours.

In step (b) of the process according to the invention the produced lansoprazole can optionally be recovered from the reaction mixture of step (a). This is preferably effected by use of at least one and most preferred by use of all of the following steps:

(i) adding a solution of a thiosulphate salt and a base to the reaction mixture of step (a),
(ii) adding water to the mixture of step (i) to precipitate solid lansoprazole and
(iii) separating lansoprazole.

In step (i) of this recovery procedure a solution of a thiosulphate salt, preferably sodium thiosulphate dissolved in water, is added to the reaction mixture of step (a), in order to decompose any excess of hydrogen peroxide after the reaction. Moreover, an inorganic base such as sodium hydroxide or potassium hydroxide or an organic base, such as triethylamine, is added. Preferably, triethylamine is used.

In step (ii) water is added to the mixture of step (a) to precipitate lansoprazole, which can be separated in a conventional manner in step (iii).

In a preferred embodiment of step (iii), the lansoprazole obtained in step (ii) is filtered of and recrystallized. Preferably, recrystallization is performed in a mixture of water and an organic solvent. As organic solvent an alkanol, such as ethanol, 1-methyl-2-pyrrolidone, N,N-dimethylacetamide, N,N-dimethylformamide or a mixture thereof can be used. In particular, a mixture of water and 1-methyl-2-pyrrolidone with a ratio of 9:1 to 1:3 (vol/vol) is used. It is also preferred that the recrystallization is carried out in a mixture of water and ethanol in the presence of a weak base, such as triethylamine or ammonia.

Furthermore, in step (iii) the recrystallized lansoprazole can be suspended in water, preferably at a temperature of 15 to 20° C. and stirred for a certain period of time, such as 2 hours. The obtained product can be collected by filtration and dried, e.g. under reduced pressure at a temperature of 40° C.

In a preferred embodiment, the water used for the suspension of lansoprazole has a pH of 8 to 11 which can be adjusted by the addition of a base, such as sodium hydroxide, potassium hydroxide, triethylamine or ammonia. Further, it is preferred that the suspension of lansoprazole in water is slowly cooled to 5° C. before filtration. It is also preferred that the maceration step is carried out several times, in order to enhance the purity of the lansoprazole.

The invention also relates to a process for preparing solid lansoprazole comprising (a') providing a solution of lansoprazole in a solvent, (b') precipitating lansoprazole from the solution of (a'), (c') separating and optionally washing the precipitated lansoprazole, (d') suspending the precipitated lansoprazole of step (c') in a solvent at a temperature of less than 25° C., preferably less than 20° C. and most preferably from 15 to 20° C., and (e') stirring the suspension of (d') and separating the obtained lansoprazole.

In step (a'), a solution of lansoprazole is provided. Preferably, lansoprazole is suspended in water, ethanol, acetone or a mixture thereof and heated to give a solution of lansoprazole. In particular, a mixture of water and ethanol is used. Preferably, the solvent or solvent mixture further comprises a base selected from sodium hydroxide, potassium hydroxide, triethylamine or ammonia. It is also preferred that the dissolution temperature does not exceed 55° C. Any insoluble residues can be filtered off.

In another preferred embodiment of step (a'), lansoprazole is dissolved in 1-methyl-2-pyrrolidone.

In step (b'), lansoprazole is precipitated from the solution of (a'). Preferably, the solution of step (a') is cooled and stirred to effect the crystallization of lansoprazole. It is also possible to effect the precipitation of lansoprazole by the addition of water. Preferably, the solution is vigorously stirred when the crystallization of lansoprazole starts. It is further preferred that the solution is gradually cooled to a temperature of 20° C. and more preferably to a temperature of from 0 to 5° C. In particular, the solution is cooled within 20 minutes to a temperature of from 35 to 40° C., then within one hour to a temperature of 20° C. and finally within one hour to a temperature of from 0 to 5° C. Moreover, it is preferred that the resulting suspension of lansoprazole is stirred for an additional period of time ranging from 0.5 to 10 hours.

In step (c') lansoprazole is separated and preferably washed with a solvent or solvent mixture comprising water, ethanol, acetone or a mixture thereof. In a preferred embodiment, solid lansoprazole is filtered off and washed with a cold mixture of water and ethanol (1:9 vol/vol).

In step (d'), the lansoprazole obtained in step (c') is suspended in a solvent or mixture of solvents. Preferably, water, potable water, ethanol, acetone or a mixture thereof is used. In a preferred embodiment, lansoprazole is suspended in water having a pH value ranging from 8 to 11, preferably from 9 to 10 and more preferably from 9.25 to 9.75. The pH of the solvent can preferably be adjusted by a base such as sodium hydroxide, potassium hydroxide, triethylamine or ammonia. The temperature of the suspension of step (d') is less than 25° C., preferably less than 20° C. and more preferably between 15 to 20° C. In particular, a temperature of about 20° C. is used.

Finally, in step (e') the obtained suspension is stirred for a certain period of time ranging from 0.5 to 10 hours, preferably for 2 hours. During this stirring the temperature is preferably in the range from 15 to 25° C. and more preferably about 20° C. In a preferred embodiment, the suspension is then cooled in one hour to a temperature of 5° C. The lansoprazole can be filtered off or collected by centrifugal filtration and preferably washed with a solvent or solvent mixture comprising water having a pH of 9.0 to obtain wet lansoprazole. It is further preferred that steps (d') and (e') are repeated to obtain lansoprazole of a higher purity. Finally, the wet lansoprazole can be dried in a vacuum at a slightly elevated temperature such as about 40° C.

The solvents used in step (a') and (d') can independently be selected from water, ethanol, acetone or mixtures thereof, i.e. the solvent used in step (a') can be identical or different from the solvent used in step (d').

The solvents used in steps (a'), (c') and (d') can independently from each other comprise a base, preferably sodium hydroxide, potassium hydroxide, triethylamine or ammonia.

It has surprisingly been found out that the solid lansoprazole obtained by a process involving steps (a') to (e') has an unexpectedly high BET-surface area. Preferably, the BET-surface area of the prepared lansoprazole is from 1.5 to 7.0 $m^2/g$ and more preferably from 2.5 to 5.2 $m^2/g$ and the invention also relates to such a lansoprazole.

Unless otherwise noted, the BET-surface areas of the produced lansoprazole are determined by calculation from desorption data of nitrogen obtained on a BET FlowSorb II 2300 (Micromeritics Instrument Corp., USA) using a mixture of 30 vol. % nitrogen and 70 vol. % helium at 77 K.

It is a further advantage of the process according to the invention that lansoprazole having a high BET-surface area in the range from 1.5 to 7.0 $m^2/g$ is directly obtained in the crystallization procedure and thus, no need for further treatment of the crystallized product exists to obtain such a surface area.

Accordingly, the lansoprazole obtained by the process of the invention is particularly suitable for inclusion in pharmaceutical compositions. The invention therefore, also relates to pharmaceutical compositions comprising lansoprazole having a BET-surface area of 1.5 to 7.0 $m^2/g$.

Preferably, the pharmaceutical compositions comprise, besides lansoprazole, at least one excipient selected from a stabilizer, a filler, a disintegrant, a wetting agent, a carrier and a binder. The pharmaceutical compositions can also be further coated by a separating layer and/or a gastro-resistant coating.

Preferably, the stabilizer is selected from the group consisting of alkaline and earth alkaline metal carbonates such as sodium carbonate and magnesium carbonate or magnesium carbonate heavy, alkaline metal phosphates such as disodium hydrogen phosphate and trisodium phosphate, glucosamine, alkaline reacting aminoacids, natural silicates and mixtures thereof.

Furthermore, the filler is preferably selected from the group consisting of microcrystalline cellulose, sucrose, starch, lactose, mannitol, sorbitol and mixtures thereof.

In a preferred embodiment, the disintegrant is selected from the group consisting of starch, starch derivatives such as sodium starch glycolate and pregelatinized starch, low-substituted hydroxypropyl cellulose, crospovidone, polacrilin potassium, croscarmellose sodium and mixtures thereof.

In a further embodiment, the wetting agent is preferably selected from the group consisting of sodium dodecyl sulfate, polyoxyethylene sorbitan fatty acid esters, poloxamers and mixtures thereof.

In a preferred embodiment, the carrier is selected from the group consisting of sugar beads, such as neutral pellets made of sucrose and starch, and microcrystalline cellulose beads.

It is also preferred that the binder is selected from the group consisting of polyvinyl pyrrolidone, hydroxypropyl cellulose, hydroxypropylmethyl cellulose, hydroxyethyl cellulose, methyl cellulose and mixtures thereof.

It was surprisingly found out that the pharmaceutical compositions according to the invention show a fast release of lansoprazole. The release of lansoprazole was spectrophotometrically determined using Hewlett Packard 8452 A Diode array spectrophotometer and automatic sampling system Multicell Transport System. Dissolution profiles were obtained at 37° C. using 900 ml phosphate buffer solution having pH 6.8 and Ph. Eur. Paddle method (100 rpm). Before analysis, the pellet samples were treated with artificial gastric juice (500 ml) having a pH of 1.2 for one hour, washed and quantitatively transferred into the phosphate buffer. The result of this test is displayed in FIG. 1 showing the release of lansoprazole having different surface areas from pellets. The release of lansoprazole having a BET-surface area of 4.67 $m^2/g$ is clearly faster compared to that of lansoprazole having a BET-surface area of 0.87 $m^2/g$ and 1.00 $m^2/g$, respectively. Preferably more than 80%, more preferably more than 85% and most preferred more than 90% of lansoprazole are released from the compositions according to the invention within 30 minutes.

The pharmaceutical compositions according to invention can be in form of pellets, tablets, capsules, sachets, powders, granulates and aggregates. The dosage form of a tablet or pellets filled into capsules or sachets is preferably used.

In a preferred embodiment, the pharmaceutical composition comprises pellet cores, optionally a separating coating, an enteric coating and optionally an overcoat.

Suitable pellet cores are formed from powders comprising lansoprazole and at least one excipient by extrusion-spheronization or direct pelletization in a high-shear mixer or a rotor granulator. Alternatively, said pellet cores can also be formed by coating of inert cores prepared from sucrose, starch, microcrystalline cellulose, lactose or mixtures thereof.

A convenient manner of coating the inert cores with lansoprazole is the "powder layering" process performed in centrifugal equipment, i.e. rotor fluid bed equipment (e.g. a Glatt Rotor Granulator), or a coating pan (e.g. Pellegrini Coating Pan, GS Coating System). For this purpose, the inert cores are moistened with a solution of binder, and then lansoprazole together with other excipients is added as a powder, and the layered pellets are dried in the same equipment in which the coating is performed or in other specialized equipment for drying, such as a drying chamber with or without vacuum. The coating of lansoprazole can also be effected in the "suspension layering" process by spraying the lansoprazole suspension onto inert cores in a fluid bed coater granulator.

Preferably, the enteric coating of pharmaceutical compositions of the invention comprises (A') at least one enteric-insoluble polymer selected from the group consisting of methacrylic acid copolymers, cellulose derivatives such as hydroxypropylmethyl cellulose phthalate and hydroxypropylmethyl cellulose succinate and polyvinyl acetatephthalate, (B') at least one plasticizer selected from the group consisting of triethyl citrate, polyethylene glycol, triacetin and mixtures thereof, (C') at least one antitacking agent such as talc or glyceryl monostearate, (D') pigments and/or (E') at least one wetting agent selected from the group consisting of sodium dodecyl sulfate, polyoxyethylene, sorbitan fatty acid esters, poloxamers and mixtures thereof.

Preferably, the thickness of the enteric coating is 20-60 μm and in particular 25-50 μm.

Optionally, the final enteric coated pellets can additionally be thermally treated. This post-drying procedure is carried out for 2-24 hours at an elevated temperature from 30 to 50° C., preferably from 35 to 45° C., and more preferably from 38 to 42° C., in a suitable type of dryer, e.g. a tray dryer or a vacuum dryer.

In a further embodiment, enteric coated pellet cores can comprise one or more separating layers. The separating layer (s) comprise at least one of water-soluble polymers, alkaline reacting compounds such as alkaline or earth alkaline metal carbonates, alkaline metal phosphates, glucosamine, alkaline reacting aminoacids, natural silicates, talc, plasticizers, such as propylene glycol, coloring agents, such as pigments (e.g. iron oxide, titanium dioxide) and mixtures thereof.

The pharmaceutical compositions of the invention may be further coated by an overcoat to increase the plasticity of the pellet surface.

Preferably, the components forming the enteric coating or the overcoating are mixed with purified water to give a suspension. This suspension is preferably sprayed in a fluidized-bed equipment on pellet cores. To avoid settling, the mixture is stirred during the spraying process.

The obtained coated pellets can be used for the production of capsules, sachets and tablets which can also be orally fast-disintegrating tablets.

The invention is in the following explained in more detail with reference to examples and a FIGURE.

EXAMPLE 1

Preparation of 2-[[[3-methyl-4-(2,2,2-trifluoroethoxy)-2-pyridinyl]methyl]thio]-1H-benzimidazole a) 2,3-Dimethylpyridine N-oxide 46.2 g of magnesium monoperoxyphthalate hexahydrate in 150 ml of water were slowly added at room temperature to a solution of 11.32 ml (0.100 mole) of 2,3-dimethylpyridine and 11.2 g of potassium carbonate in 50 ml of water. The reaction was carried out at a pH of 6.5-7.0, adjusted by a solution of potassium carbonate, and the reaction mixture was stirred for three hours at a temperature of from 25 to 30° C. At the end of the reaction, the pH was adjusted to 7.5-8.0, 40 g of sodium chloride were added and the 2,3-dimethylpyridine N-oxide was extracted with methylene chloride. The extraction was repeated from saturated reaction solution. The combined organic phases were dried with sodium sulphate and concentrated to a volume of 60 ml. The yield was 97-98%, determined by HPLC.

b) 2,3-Dimethyl-4-nitropyridine N-oxide

The solution of 2,3-dimethylpyridine N-oxide in 60 ml of methylene chloride obtained in the previous step was cooled to −10° C., then 34.3 ml of conc. sulphuric acid were added dropwise at a temperature of from −10 to 10° C. and methylene chloride was distilled off. 14.14 g of potassium nitrate in 70 ml of sulphuric acid were added to the reaction mixture which was then heated to 80-85° C. and stirred for 3-4 hours. After cooling to −10° C., the mixture was poured into 500 ml of water and extracted with methylene chloride. The organic phases were dried with sodium sulphate and concentrated to a volume of 60 ml. The yield was 80-82%, determined by HPLC.

c) 2,3-Dimethyl-4-(2,2,2-trifluoroethoxy)pyridine N-oxide 13.5 ml of 2,2,2-trifluoroethanol were added to the solution of 2,3-dimethyl-4-nitropyridine N-oxide (60 ml, 0.080 mole) obtained in the previous step. Then methylene chloride was distilled off. The resulting concentrated solution was added to a solution of 14.85 g (0.133 mole) potassium tert-butoxide in 54 ml of 2,2,2-trifluoroethanol and 0.034 g of palladium(II) chloride. The reaction mixture was heated to 83-88° C. for 6-8 hours. After cooling to 30° C., potassium nitrite was filtered off, following by distillation of 2,2,2-trifluoroethanol. To this residue 17 ml of a saturated solution of sodium chloride were added and the pH was adjusted by the addition of conc. hydrochloric acid to 6.6. The product was extracted with methylene chloride and 100 ml of a saturated solution of sodium chloride. The organic phases were dried with sodium sulphate and concentrated to a volume of 40 ml. The yield was 95-97%, determined by HPLC.

d) 2-Acetoxymethyl-3-methyl-4-(2,2,2-trifluoroethoxy)pyridine 40 ml of 2,3-dimethyl-4-(2,2,2-trifluoroethoxy)pyridine N-oxide (0.078 mole) in methylene chloride were dropwise added to a solution of 28.7 ml acetanhydride and 0.182 g 4-dimethylaminopyridine, then methylene chloride was distilled off and the residue was heated to a temperature of from 90 to 95° C. for 4-5 hours. At the end of the reaction, 3.6 ml of water were added and acetic acid was removed by vacuum distillation to obtain an oil product. The yield was 94-96%, determined by HPLC.

e) 2-Hydroxymethyl-3-methyl-4-(2,2,2-trifluoroethoxy)pyridine 34.8 g of the product obtained in the previous step corresponding to 18.7 g (0.071 mole) 2-acetoxymethyl-3-methyl-4-(2,2,2-trifluoroethoxy)pyridine were dissolved at room temperature in 15 ml of a mixture of methanol/water (1:1), the pH of which was adjusted with aqueous sodium hydroxide (33%) to 13. The reaction was carried out at a temperature of from 25 to 30° C. and a pH of from 12.5 to 13.5, adjusted by the addition of sodium hydroxide. The end was determined by HPLC method. The mixture was neutralized with 36% hydrochloric acid and extracted with methylene chloride. The organic layers were dried and concentrated to 60 ml. The yield was 95-97%, determined by HPLC.

f) 2-Chloromethyl-3-methyl-4-(2,2,2-trifluoroethoxy)pyridine hydrochloride 160 ml of toluene were added to 14.9 g (0.067 mole) of 2-hydroxymethyl-3-methyl-4-(2,2,2-trifluoroethoxy)pyridine in methylene chloride followed by distillation of methylene chloride. The solution was purified with 2.7 g of activated charcoal, filtered and washed with 36 ml of toluene. To this solution 5.4 ml (0.075 mole) of thionyl chloride in 27 ml of toluene were added dropwise and maintained for 3 hours. The gas was removed under vacuum at room temperature, then the resulting mixture was cooled to a temperature of from 0 to 5° C. and stirred for one hour. The product was filtered, washed with 3 ml of toluene and dried in a vacuum dryer at 35-40° C. The yield was 15.65 g (84%).

g) 2-[[[3-Methyl-4-(2,2,2-trifluoroethoxy)-2-pyridinyl]methyl]thio]-1H-benzimidazole hydrochloride 12.71 g (0.0459 mole) of 2-chloromethyl-3-methyl-4-(2,2,2-trifluoroethoxy)pyridine hydrochloride were suspended in 322 ml of acetone in the presence of 2.52 ml N,N-dimethylacetamide. Then 7.24 g (0.0597 mole) of 2-mercaptobenzimidazole were added. The mixture was heated to reflux and stirred for 5 hours. After cooling to room temperature, the resulting suspension was filtered to obtain the wet product.

h) 2-[[[3-Methyl-4-(2,2,2-trifluoroethoxy)-2-pyridinyl]methyl]thio]-1H-benzimidazole hydrate The wet product obtained in the previous step was suspended in acetone/water, then 1.14 g of disodium EDTA were added and the pH was adjusted between 7.0-7.5 using an aqueous potassium hydroxide solution (50%). The resulting suspension was stirred for two hours at room temperature. The product was filtered off, then macerated in 220 ml of water for two hours at room temperature, once again filtered and dried in air or a vacuum dryer to obtain 15.97 g (93.6%, KF: 4.5%) of the desired product.

i) 2-[[[3-Methyl-4-(2,2,2-trifluoroethoxy)-2-pyridinyl]methyl]thio]-1H-benzimidazole 2-propanol solvate 50 g of 2-[[[3-Methyl-4-(2,2,2-trifluoroethoxy)-2-pyridinyl]methyl]thio]-1H-benzimidazole hydrate was suspended in 250 ml of 2-propanol, heated to reflux and the resulting solution was hot filtered. The product was crystallized, filtered and dried in a vacuum drier at 50° C. to obtain 50 g of the solvated form (LOD: 14.5%, KF: 0.08%).

j) 2-[[[3-Methyl-4-(2,2,2-trifluoroethoxy)-2-pyridinyl]methyl]thio]-1H-benzimidazole 50 g of 2-[[[3-Methyl-4-(2,2,2-trifluoroethoxy)-2-pyridinyl]methyl]thio]-1H-benzimidazole 2-propanol solvate was dried at 80° C. in a vacuum dryer to obtain 43.62 g of the desolvated form.

EXAMPLE 2

Preparation of 2-[[[3-methyl-4-(2,2,2-trifluoroethoxy)-2-pyridinyl]methyl]sulfinyl]-1H-benzimidazole (lansoprazole)

a) (i) 40 g (0.108 mole) 2-[[[3-methyl-4-(2,2,2-trifluoroethoxy)-2-pyridinyl]methyl]thio]-1H-benzimidazole hydrate was dissolved in 120 ml of 1-methyl-2-pyrrolidone (NMP) at room temperature, then 0.263 g (1.077 mmole) of vanadium(V) oxytriisopropoxide were added and the reaction mixture was cooled to a temperature of from 0 to 5° C. 12.96 g (0.138 mole) of hydrogen peroxide urea adduct were suspended (optionally per partes) and the reaction was carried out at a temperature of from 0 to 10° C. for half an hour and then at a temperature of from 10 to 15° C. until the reaction was completed. At the end of the reaction, 5 ml of triethylamine and a solution of 5.68 g of sodium thiosulphate pentahydrate in 6 ml of water were added. The product was precipitated with water (280 ml at 20±5° C.) and filtered off to obtain 48.3 g of wet lansoprazole.

(ii) 40 g (0.1077 mole) 2-[[[3-methyl-4-(2,2,2-trifluoroethoxy)-2-pyridinyl]methyl]thio]-1H-benzimidazole hydrate was suspended in 240 ml of ethanol and 0.264 g (1.077 mmole) vanadium(V) oxytriisopropoxide dissolved in 1 ml of ethanol were added at room temperature (20-25° C.). The suspension was cooled to 10-12° C. and 12.14 g (0.129 mole) hydrogen peroxide urea adduct were added. The reaction was carried out at 10-15° C. for two hours and then at 5-10° C. until the reaction was completed. At the end of the reaction (3-6 hours, depending upon the temperature), 6 g of sodium thiosulphate pentahydrate in a solution of 40 ml water and 120 ml ethanol were added at 5-10° C., the mixture was stirred for one hour at 10-15° C. and 0.5 ml of 30% aqueous solution of sodium hydroxide were added to achieve a pH of about 10. The suspension was heated to 50-55° C., hot filtered and then gradually cooled to room temperature in one hour and then to 5-10° C. in half to one hour and agitated at that temperature for another one hour. The product was filtered off to obtain 48 g of wet lansoprazole.

b) 20 g (0.0538 mole) of 2-[[[3-methyl-4-(2,2,2-trifluoro-ethoxy)-2-pyridinyl]methyl]thio]-1H-benzimidazole hydrate were dissolved in 60 ml of 1-methyl-2-pyrrolidone (NMP) at room temperature, then 0.080 g (0.6 mmole) vanadium(V) oxytrifluoride were added and the reaction mixture was cooled to a temperature of from 0 to 5° C. 8.1 g (0.0861 mole) of hydrogen peroxide urea adduct were suspended (optionally per partes) and the reaction was carried out at a temperature of from 0 to 10° C. for half an hour then at a temperature of from 10 to 15° C. until the reaction was completed. At the end of the reaction 0.5 ml of triethylamine and a solution of 11.36 g sodium thiosulphate pentahydrate in 12 ml of water were added. The product was precipitated with water (120 ml at 20±5° C.) and filtered off to obtain 16.8 g of wet lansoprazole.

c) 20 g (0.0538 mole) of 2-[[[3-methyl-4-(2,2,2-trifluoro-ethoxy)-2-pyridinyl]methyl]thio]-1H-benzimidazole hydrate was dissolved at room temperature in 60 ml of 1-methyl-2-pyrrolidone (NMP) and the reaction mixture was cooled to a temperature of from 0 to 5° C. 12.07 g (0.070 mole) of 3-chloroperbenzoic acid were suspended (optionally per partes) and the reaction was carried out at a temperature of from 0 to 10° C. for half an hour, then at 10-15° C. until the reaction was completed. At the end of the reaction 0.5 ml of triethylamine and a solution of 11.36 g sodium thiosulphate pentahydrate in 12 ml of water were added. The product was precipitated with water (120 ml at 20±5° C.) and filtered off to obtain 21 g of wet lansoprazole.

d) Example 2d) was repeated except that at the end of the reaction 2 ml of sodium hydroxide (30% aq.) and a solution of 6.0 g of sodium thiosulphate pentahydrate in 6 ml of water were added. The product was precipitated with water (280 ml at 20±5° C.) and filtered off to obtain 59.4 g of wet lansoprazole.

e) Purification of Lansoprazole i) 48 g of wet lansoprazole was dissolved in 80 ml of 1-methyl-2-pyrrolidone (NMP) and 5 ml of triethylamine, cooled to 15° C. and the product was precipitated with 240 ml of water. The suspension was stirred for 4-10 hours and filtered to obtain 34.9 g wet lansoprazole. The wet crystallized product was suspended in 200 ml of water treated with triethylamine so that the pH value was adjusted to about 9-10. The suspension was cooled down to 15° C., stirred at a temperature of from 15 to 20° C. for 2 hours and then cooled to a temperature of from 0 to 5° C. The obtained crystals were collected by centrifugal filtration and dried under reduced pressure at 40° C. to obtain 26.6 g of lansoprazole form A.

ii) Example 2e) i) was repeated with the exception that the pH of the suspension of wet lansoprazole was adjusted by sodium hydroxide instead of triethylamine.

iii) Example 2e) i) was repeated with the exception that wet crystallized lansoprazole was suspended in potable water instead of water having a pH of 9 to 10.

iv) 48 g wet lansoprazole were dissolved in a mixture of 110 ml 1-methyl-2-pyrrolidone (NMP), 2.67 g sodium hydroxide and 75 ml i-propyl acetate at 20±2° C. The resulting layers were separated, the aqueous phase was cooled to 10° C. and the product was precipitated by addition of 8.3 ml of 50% acetic acid to give a pH value between 9.8 and 10.1 at 5-10° C. The suspension was stirred for two hours at 5-10° C., then filtered, and washed with 20 ml of water to obtain 36.8 g of wet lansoprazole. The wet crystallized product was suspended in 228 ml of water having a pH value of about 9-10 (treated with sodium hydroxide) at 16-18° C., stirred for two hours and cooled to 5° C. The product was filtered, washed with 10 ml of water and dried under reduced pressure at 40° C. to obtain 26.7 g of lansoprazole form A.

v) Example 2. e. iv. was repeated with the exception that formic acid was used instead of acetic acid.

vi) Example 2. e. iv. was repeated with the exception that hydrochloric was used instead of acetic acid.

EXAMPLE 3

Purification of Lansoprazole (Comparative)

1.12 kg of wet crude lansoprazole were suspended in an ethanol/water/triethylamine mixture (6.5:0.7:0.025 l) and the mixture was heated to 45° C. The insoluble material was filtered off, the filtrate was gradually cooled and when the crystallization started (32° C.), the suspension was vigorously stirred and cooled to 0° C. The suspension was stirred for an additional half an hour. The solid was filtered to obtain 0.87 kg of wet product which was suspended in 4.0 l of ethanol with 0.022 ml of triethylamine at 32° C. The suspension was heated to 45° C. to obtain a clear solution, then gradually cooled to 5° C. and stirred for one hour at 0° C. Finally, the product was filtered, washed with 0.4 l of cold ethanol and a mixture of 0.1 l of ethanol and 0.5 ml of triethylamine and dried at 40° C. to obtain 0.41 kg of lansoprazole form A having a BET-surface area of 0.25 m$^2$/g.

The lansoprazole was further milled to obtain a solid with a BET-surface area of 0.87 m$^2$/g.

EXAMPLE 4

Purification of Lansoprazole 1.58 kg of wet crude lansoprazole were suspended in an ethanol/water/ammonia mixture (5.2:0.6:0.006 l) and the mixture was heated to 50° C. The insoluble material was filtered off, the filtrate was gradually cooled and when the crystallization started (32° C.), the suspension was vigorously stirred and cooled to 0° C. The suspension was stirred for an additional half an hour. The solid was filtered, washed with 1.0 l of a cold ethanol/water mixture (9:1) to obtain 1.19 kg of wet product which is suspended at 22° C. in 6.65 l of water with a pH of 9.66 adjusted with triethylamine. The suspension was stirred for two hours at 20±2° C., then cooled in one hour to 5° C., filtered and washed with 1.0 l of water with a pH of 9.0 to obtain 1.55 kg of wet product. Maceration in water was once again repeated. The wet product (1.48 kg) was dried in vacuo at 40° C. to give 0.71 kg of lansoprazole form A having a BET-surface area of 4.67 m$^2$/g.

EXAMPLE 5

Purification of Lansoprazole (Comparative)

Example 4 was repeated with the exception that the temperature of the suspension of lansoprazole in water is 30° C. instead of 20±2° C. 0.76 g of lansoprazole form A having a BET-surface area of 1.0 m$^2$/g was obtained.

EXAMPLE 6

Preparation of Pellets Comprising Lansoprazole

The lansoprazole used in this example was prepared according to any one of examples 2 or 4.

First, 66.0 g of polyvinyl pyrrolidone K-30 were dissolved in 500.0 g of purified water. 57.8 g of disodium hydrogen phosphate dihydrate were dissolved in 500.0 g of purified water and then added to the solution of polyvinyl pyrrolidone. Then, 247.5 g of lansoprazole, 279.7 g of sucrose and 174.0 g of maize starch were added to the resulting solution and this dispersion was homogenized with an appropriate mixer/homogenizer until a substantially homogeneous suspension was obtained. Finally, 25.0 g of sodium dodecyl sulfate were dissolved in 160.0 g of purified water and added into the suspension while gently stirring. The obtained suspension was then sprayed onto 1100.00 g of inert cores (neutral pellets made from starch and sucrose, 710-850 μm) in a Wurster fluidized-bed equipment to form cores having a first layer.

Such coated cores were additionally coated with a dispersion containing 1500.0 g of Eudragit L-30D, 45.0 g of polyethylene glycol 6000, 144.0 g of talc, 43.5 g of titanium dioxide and 1500.0 g of water. First, Eudragit L-30D dispersion was diluted with 1160.0 g of water. Then, the suspension of talc and titanium dioxide in 240.0 g of water was added. Finally, the solution of polyethylene glycol in 100.0 g of water was added to give the dispersion for coating.

EXAMPLE 7

Preparation of Pellets Comprising Lansoprazole

Example 6 was repeated except that between both coatings a separating layer was applied.

For this purpose, 20.0 g of polyvinyl pyrrolidone K-30 were dissolved in 300.0 g of purified water. Then, 10.0 g of disodium hydrogen phosphate dihydrate were dissolved in 150.0 g of purified water and added to the solution of polyvinyl pyrrolidone. Finally, 10.0 g of talc were suspended in the solution. The obtained suspension was sprayed onto cores having the first layer.

Pellets coated with a separating layer were finally coated with an enteric coating using the same procedure as described in Example 6.

EXAMPLE 8

Preparation of Pellets Comprising Lansoprazole

First, 27.8 g of hydroxypropyl cellulose were dissolved in 1350.0 g of purified water. Then, 213.0 g of magnesium carbonate heavy, 555.5 g of sucrose, 347.1 g of maize starch and 300.0 g of lansoprazole were suspended in the solution. Finally, 27.3 g of sodium dodecyl sulfate were dissolved in 100.0 g of purified water and added to the suspension while gently stirring. 1018.3 g of inert cores (neutral pellets, made from starch and sucrose, 710-850 μm) were coated with the above prepared suspension to form cores with a first layer.

Such coated cores were additionally coated with a separating layer. First, 96.9 g of hydroxypropyl methylcellulose 6 cp was dissolved in 1780.0 g of water and then 145.3 g of magnesium carbonate heavy was suspended in the solution to give the suspension for coating.

Pellets having such a separating layer were additionally coated with a dispersion containing 1450.0 g of Eudragit L-30D, 43.4 g of polyethylene glycol 6000, 85.2 g of talc, 25.6 g of titanium dioxide and 1450.0 g of water. First, Eudragit L-30D dispersion was diluted with 1190.0 g of water. Then, the suspension of talc and titanium dioxide in 160.0 g of water was added. Finally, the solution of polyethylene glycol in 100.0 g of water was added while stirring to give the dispersion for manufacturing the enteric-coated pellets.

The release of lansoprazole from pellets prepared according to this example is shown in the FIG. 1. If a lansoprazole prepared according to example 4 having a BET-surface area of 4.76 $m^2/g$ is used, more than 90% of the drug is released within the first 30 minutes (upper curve). The use of a lansoprazole described in examples 3 and 5 having a BET-surface area of 0.87 $m^2/g$ and 1.0 $m^2/g$, respectively, results in a clearly smaller release of lansoprazole.

Thus, it has been shown that lansoprazole having a BET-surface area according to the invention is particularly suitable for the preparation of pharmaceutical compositions showing a fast release of lansoprazole.

EXAMPLE 9

Preparation of Pellets Comprising Lansoprazole

The lansoprazole used in this example was prepared according to any one of examples 2 or 4.

Example 8 was repeated with the exception that hydroxypropyl cellulose was dissolved in 1100.0 g of purified water and sodium dodecyl sulfate was dissolved in 200.0 g of purified water. Moreover, no separating layer was applied on the cores having a first layer.

Furthermore, for preparing an overcoat a dispersion containing 2285.6 g of Eudragit L-30D, 68.6 g of polyethylene glycol 6000, 142.9 g of talc, 42.9 g of titanium dioxide, 4.1 g of sodium hydroxide and 2200.0 g of water was used. First, Eudragit L-30D dispersion was diluted with 1160.0 g of water. Then, the suspension of talc and titanium dioxide in 150.0 g of water was added. The solution of polyethylene glycol in 300.0 g of water was added to the obtained suspension to give the dispersion to which finally a solution of sodium hydroxide in 120 g of water was added. The obtained dispersion was sprayed onto cores having a first layer.

EXAMPLE 10

Preparation of Pellets Comprising Lansoprazole

Example 6 was repeated except that 28.9 g of disodium hydrogen phosphate dihydrate were used instead of 57.8 g.

EXAMPLE 11

Preparation of Pellets Comprising Lansoprazole

Example 6 was repeated with the exception that the pellet cores having a first layer were additionally coated with a dispersion containing 1500.0 g of Eudragit L-30D, 22.5 g of polyethylene glycol 6000, 144.0 g of talc, 45.0 g of triethyl citrate, 43.5 g of titanium dioxide and 1500.0 g of water. First, Eudragit L-30D dispersion was diluted with 1160.0 g of water. Then, the suspension of talc and titanium dioxide in 240.0 g of water was added. Polyethylene glycol 6000 was dissolved in 100.0 g of water and then triethyl citrate was dispersed in this solution. The obtained dispersion was finally added to the suspension of Eudragit L-30D, talc and pigment to give the dispersion which was sprayed onto cores having the first layer.

EXAMPLE 12

Preparation of Pellets Comprising Lansoprazole

The lansoprazole used in this example was prepared according to any one of examples 2 or 4.

First, 99.0 g of hydroxypropyl cellulose were dissolved in 2000.0 g of purified water. 450.0 g of lansoprazole and 315.0 g of magnesium carbonate heavy were added to the resulting solution and the dispersion was homogenised with an appropriate mixer until a substantially homogeneous dispersion was obtained. Then, 40.5 g of sodium dodecyl sulfate were dissolved in 400.0 g of purified water. This solution was added to the dispersion which was subsequently homogenised. The obtained dispersion was then sprayed onto 1500.00 g of inert cores (neutral pellets, made from starch and sucrose) in a Wurster fluidized-bed equipment to form cores having a first layer. 2083.9 g of coated cores were then coated with a dispersion containing 83.4 g of polyvinyl pyrrolidone K-30, 195.0 g of magnesium carbonate heavy and 1300.0 g of purified water.

1998.8 g of such coated pellets were additionally coated with a dispersion containing 1665.7 g of Eudragit L-30D, 50.0 g of polyethylene glycol 6000, 166.6 g of talc, 29.4 g of titanium dioxide and 1499.1 g of water.

EXAMPLE 13

Preparation of Pellets Comprising Lansoprazole

Example 12 was repeated except that for preparing cores having a first layer additionally 375.0 g of sucrose and 225.0 g of maize starch were added to the solution of hydroxypropyl cellulose.

2603.9 g of such coated cores were then coated with a dispersion which contained 104.2 g of polyvinyl pyrrolidone, 195.0 g of magnesium carbonate heavy and 1666.5 g of purified water.

2456.4 g of such coated pellets were additionally coated with a dispersion containing 1637.6 g of Eudragit L-30D, 49.1 g of polyethylene glycol 6000, 163.8 g of talc, 28.9 g of titanium dioxide and 1473.9 g of water.

EXAMPLE 14

Preparation of Pellets Comprising Lansoprazole

Neutral pellets made from microcrystalline cellulose were used instead of neutral pellets made from starch and sucrose as inert cores which were coated by the procedure of Example 12.

EXAMPLE 15

Preparation of Pellets Comprising Lansoprazole

The lansoprazole used in this example was prepared according to any one of examples 2 or 4.

First, 28.6 g of hydroxypropyl cellulose were dissolved in 800.0 g of purified water. Then, 230.4 g of magnesium carbonate heavy, 600.0 g of sucrose, 375.0 g of maize starch and 300.0 g of lansoprazole were suspended in the solution. Finally, 29.5 g of sodium dodecyl sulfate were dissolved in 100.0 g of purified water and added to the suspension while gently stirring. 1071.4 g of inert cores (neutral pellets made from starch and sucrose) were placed into the product container of a Wurster fluidized-bed equipment and coated with the above prepared suspension to form cores with a having layer.

Such coated cores were additionally coated with a separating layer. First, 114.3 g of hydroxypropyl methylcellulose 6 cp were dissolved in 1780.0 g of water and then 171.4 g of magnesium carbonate heavy were suspended in this solution to give the suspension for coating.

Pellets having such a separating layer were additionally coated with a dispersion containing 1450.0 g of Eudragit L-30D, 43.4 g of polyethylene glycol 6000, 85.2 g of talc, 25.6 g of titanium dioxide, 2.73 g of sodium hydroxide and 1450.0 g of water. First, Eudragit L-30D dispersion was diluted with 1110.0 g of water. Then, the suspension of talc and titanium dioxide in 160.0 g of water was added. Finally, solution of polyethylene glycol in 100.0 g of water and solution of sodium hydroxide in 80.0 g of water were added while stirring to give the dispersion for manufacturing the enteric-coated pellets.

EXAMPLE 16

Preparation of Pellets Comprising Lansoprazole

Neutral pellets made from microcrystalline cellulose were used as inert cores instead of those made from starch and sucrose and were then coated by the procedure of Example 13.

EXAMPLE 17

Preparation of Pellets Comprising Lansoprazole

The lansoprazole used in this example was prepared according to any one of examples 2 or 4.

100.0 g of lansoprazole, 15.0 g of magnesium carbonate heavy, 150.0 g of microcrystalline cellulose, 465.0 g of sucrose, 200.0 g of crospovidone and 70.0 g of polyvinyl pyrrolidone K-30 were mixed, 330.0 g of water was added and the mixture was granulated in a high-shear mixer. The mixture was extruded and then spheronized. The obtained pellet cores were dried in a fluidized-bed equipment or a chamber dryer at a temperature of inlet air from 35° C. to 40° C. until the weight loss of drying was less than 1.5%.

Such pellet cores were additionally coated in a Wurster fludized-bed equipment to manufacture enteric-coated pellets. A dispersion which contained 833.4 g of Eudragit L-30D, 25.0 g of polyethylene glycol 6000, 83.4 g of talc, 14.7 g of titanium dioxide and 750.0 g of water was sprayed onto 1000.0 g of pellet cores.

EXAMPLE 18

Preparation of Pellets Comprising Lansoprazole

The lansoprazole used in this example was prepared according to any one of examples 2 or 4.

The ingredients given below were mixed well, water was added and the mixture was granulated in a high-shear mixer. The granules were then dried at 50° C. for 2 hours.

Composition per 22.964 kg of granulate:

| | |
|---|---|
| Sucrose: | 16.200.0 g |
| Mannitol: | 5400.0 g |
| Xanthan gum: | 486.0 g |
| Polyvinyl pyrrolidone: | 600.0 g |
| Aerosil: | 75.0 g |
| Titanium dioxide: | 6.75 g |
| E172: | 6.75 g |
| Citric acid: | 67.5 g |
| Strawberry flavour: | 121.5 g |
| Water: | 865.0 g |

5.1 g of the resulting granules and fluidized-bed manufactured enteric-coated pellets from whichever above described Example 6 to 17 in an amount which contains 30.0 mg of lansoprazole were filled in sachets which are intended for preparation an oral suspension with 30 mL of water.

EXAMPLE 19

Preparation of Pellets Comprising Lansoprazole

The lansoprazole used in this example was prepared according to any one of examples 2 or 4.

Lansoprazole was layered on 990.0 g of neutral pellets in a rotor fluidized-bed equipment. For this purpose, 300.0 g lansoprazole, 201.6 g magnesium carbonate heavy, 450.0 g sucrose, 328.0 g maize starch and 360.0 g low-substituted hydroxypropyl cellulose were blended in an appropriate mixer to give a powder mixture. 54.0 g of hydroxypropyl cellulose were dissolved in 3000.0 g of purified water, and the solution was slowly sprayed onto the agitated batch of neutral pellets, while adding the powder mixture.

2146.9 g of such coated pellets were additionally coated in a bottom spray fluid bed coater granulator with a dispersion containing 1070.4 g Eudragit L-30D, 31.7 g polyethylene glycol 6000, 96.5 g talc, 31.7 g titanium dioxide, 14.4 g polysorbate 80 and 963.4 g purified water. After the enteric layer was built up, the pellets were additionally post-dried at 40° C. for 18 hours in a vacuum dryer.

EXAMPLE 20

Preparation of Pellets Comprising Lansoprazole

The lansoprazole used in this example was prepared according to any one of examples 2 or 4.

First, 270.0 g lansoprazole, 201.6 g magnesium carbonate heavy, 538.2 g sucrose, 328.0 g maize starch and 360.0 g low-substituted hydroxypropyl cellulose were blended in an appropriate mixer. Then, 30.2 g hydroxypropyl cellulose were dissolved in 1700.0 g purified water. 990.0 g neutral pellets were coated in a coating pan with the powder mixture while spraying the solution of hydroxypropyl cellulose.

An enteric coating was added in a fluid bed coater granulator provided with a bottom-spray system. A dispersion which contained 1040.7 g Eudragit L-30D, 30.8 g polyethylene glycol 6000, 93.8 g talc, 30.8 g titanium dioxide, 14.0 g polysorbate 80 and 936.6 g purified water, was sprayed onto 2114.0 g of pellet cores. Such enteric coated pellets were additionally post-dried at 40° C. for 24 hours in a vacuum dryer.

We claim:

1. A process for preparing lansoprazole represented by formula (I)

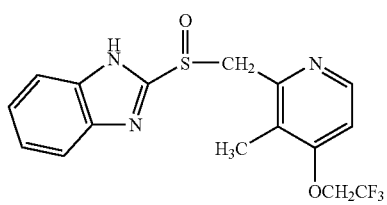

comprising
(a) reacting a compound of formula (II)

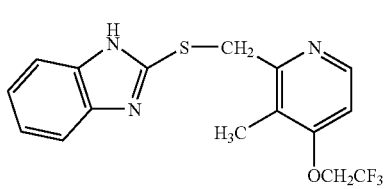

in solution with an oxidizing agent in the presence of
(A) a vanadium catalyst selected from the group consisting of vanadium(V) oxytrifluoride, vanadium(V) triesters and mixtures thereof; or
(B) acetanhydride, and
(b) optionally recovering the lansoprazole.

2. The process according to claim 1, wherein the vanadium (V) triester is vanadium(V) oxytriethoxide, vanadium(V) trioxypropoxide or vanadium(V) oxytriisopropoxide.

3. The process according to claim 1, wherein the vanadium catalyst is present in an amount of 0.001 to 0.05 equivalents, relative to compound (II).

4. The process according to claim 1, wherein said oxidizing agent is hydrogen peroxide.

5. The process according to claim 4, wherein the source of hydrogen peroxide is produced from an urea adduct of hydrogen peroxide.

6. The process according to claim 1, wherein the oxidizing agent is present in an amount of 0.5 to 3.0 equivalents relative to compound (II).

7. The process according to claim 1, wherein step (a) is performed in an organic solvent selected from the group consisting of 1-methyl-2-pyrrolidone, N,N-dimethylacetamide, N,N-dimethylformamide, alcohols and mixtures thereof.

8. The process according to claim 7, wherein the organic solvent is 1-methyl-2-pyrrolidone.

9. The process according to claim 1, wherein step (a) is carried out at a temperature ranging from 0 to 20° C.

10. The process according to claim 9, wherein the temperature is ranging from 0 to 10° C.

11. The process according to claim 1, wherein step (b) is performed by at least one of the following steps:
(i) adding a solution of a thiosulphate salt and a base to the reaction mixture of step (a),
(ii) adding water to the mixture of step (i) to precipitate solid lansoprazole and
(iii) separating lansoprazole.

12. The process according to claim 1, wherein the vanadium catalyst is present in an amount of 0.002 to 0.02 equivalents relative to compound (II).

13. The process according to claim 1, wherein the vanadium catalyst is present in an amount of 0.005 to 0.015 equivalents relative to compound (II).

14. The process according to claim 1, wherein the oxidizing agent is present in an amount of 0.7 to 2.0 equivalents relative to compound (II).

15. The process according to claim 1, wherein the oxidizing agent is present in an amount of 0.9 to 1.5 equivalents relative to compound (II).

* * * * *